(12) United States Patent
Hsiao

(10) Patent No.: US 8,714,155 B2
(45) Date of Patent: May 6, 2014

(54) MODIFIED LIQUID TRAP CUP AND A LIQUID TRAP ASSEMBLY

(75) Inventor: Fei-Fang Hsiao, Taichung (TW)

(73) Assignee: China Medical University, Taichung (TW)

( * ) Notice: Subject to any disclaimer, the term of this patent is extended or adjusted under 35 U.S.C. 154(b) by 662 days.

(21) Appl. No.: 12/985,457

(22) Filed: Jan. 6, 2011

(65) Prior Publication Data

US 2012/0017907 A1 Jan. 26, 2012

(30) Foreign Application Priority Data

Jul. 23, 2010 (TW) .............................. 99214097 U

(51) Int. Cl.
| | | |
|---|---|---|
| *A62B 7/10* | (2006.01) | |
| *A62B 23/02* | (2006.01) | |
| *A62B 9/02* | (2006.01) | |
| *A61M 16/00* | (2006.01) | |

(52) U.S. Cl.
USPC ............ 128/205.12; 128/205.27; 128/205.24; 128/204.18

(58) Field of Classification Search
USPC ................ 128/204.18, 205.27; 137/177–178; 251/322, 323, 341, 347; 4/650, 679, 4/684, 689
See application file for complete search history.

(56) References Cited

U.S. PATENT DOCUMENTS

| 4,417,574 A | * | 11/1983 | Talonn et al. ............ 128/205.12 |
|---|---|---|---|
| 4,457,305 A | | 7/1984 | Shanks et al. |
| 5,228,436 A | * | 7/1993 | Parkin ...................... 128/205.12 |
| 5,398,677 A | * | 3/1995 | Smith ....................... 128/205.12 |
| 6,484,330 B2 | * | 11/2002 | Gray et al. ......................... 4/684 |
| 7,258,322 B1 | * | 8/2007 | Yang ............................. 251/323 |
| 2006/0071189 A1 | * | 4/2006 | Cornwell et al. ................ 251/55 |
| 2010/0122702 A1 | * | 5/2010 | Reinboth et al. .......... 128/205.27 |
| 2010/0252035 A1 | * | 10/2010 | Chang ....................... 128/202.27 |
| 2010/0258129 A1 | * | 10/2010 | Huschke et al. .......... 128/205.27 |

FOREIGN PATENT DOCUMENTS

TW M376302 3/2010

OTHER PUBLICATIONS

English language translation of abstract of TW M376302.

* cited by examiner

*Primary Examiner* — Rachel Young
(74) *Attorney, Agent, or Firm* — McClure, Qualey & Rodack, LLP

(57) ABSTRACT

A liquid trap cup and a liquid trap assembly using the same are provided. The liquid trap cup comprises a hollow cup tube with a upper portion and a lower portion, a piston element with a top portion and a tail portion and a liquid discharge structure, in which the piston element is arranged airtight in the lower portion and is movable between a start point and an end point of the lower portion so as to control the opening and the closing of the liquid discharge structure. The liquid trap assembly includes the liquid trap cup and a multi-necked adapter tube with an expanded-plate structure, in which expanded-plate structure can be tightly sealed with the liquid trap. The liquid trap assembly is useful to a breathing system.

15 Claims, 11 Drawing Sheets

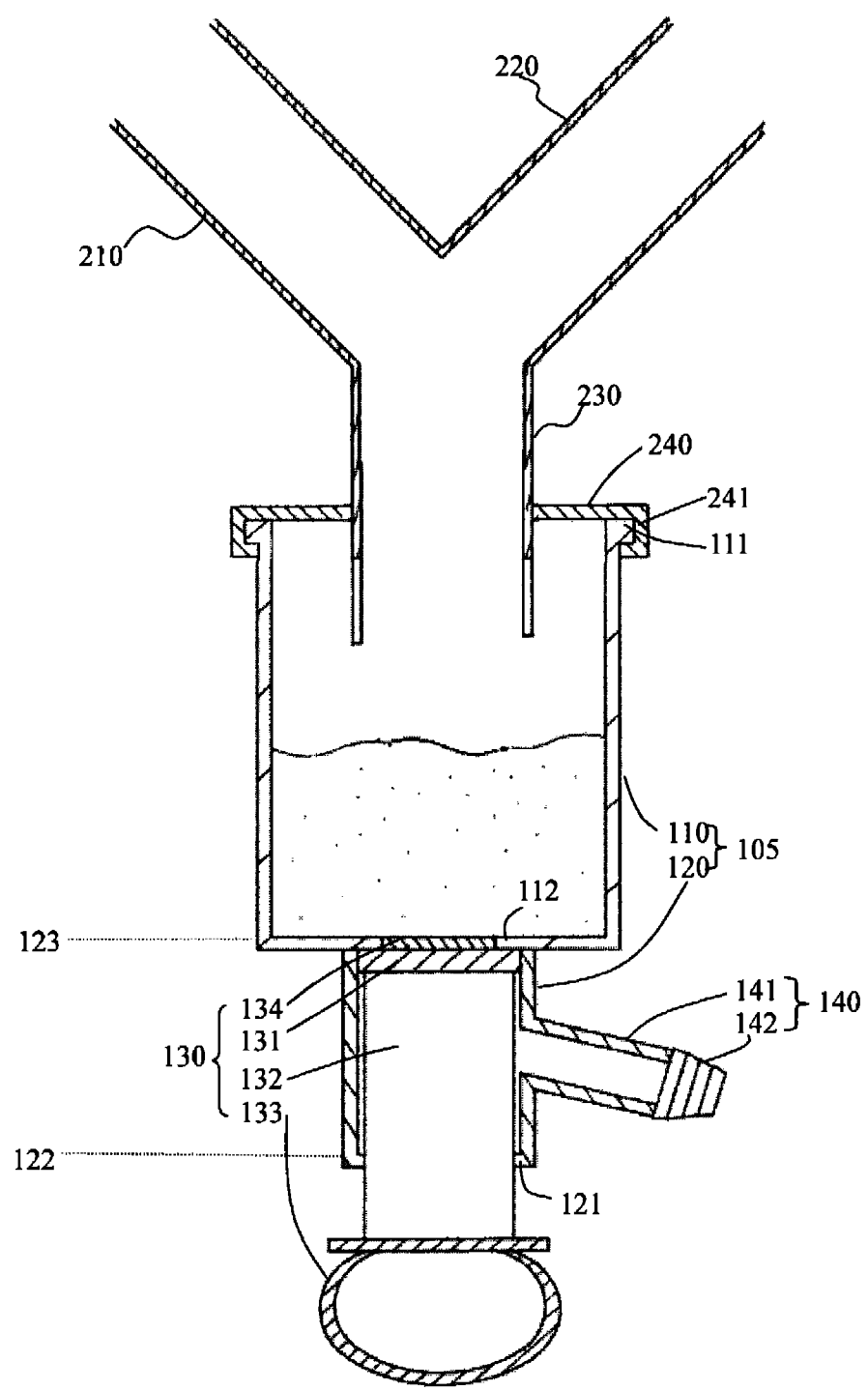

Fig.6a      100
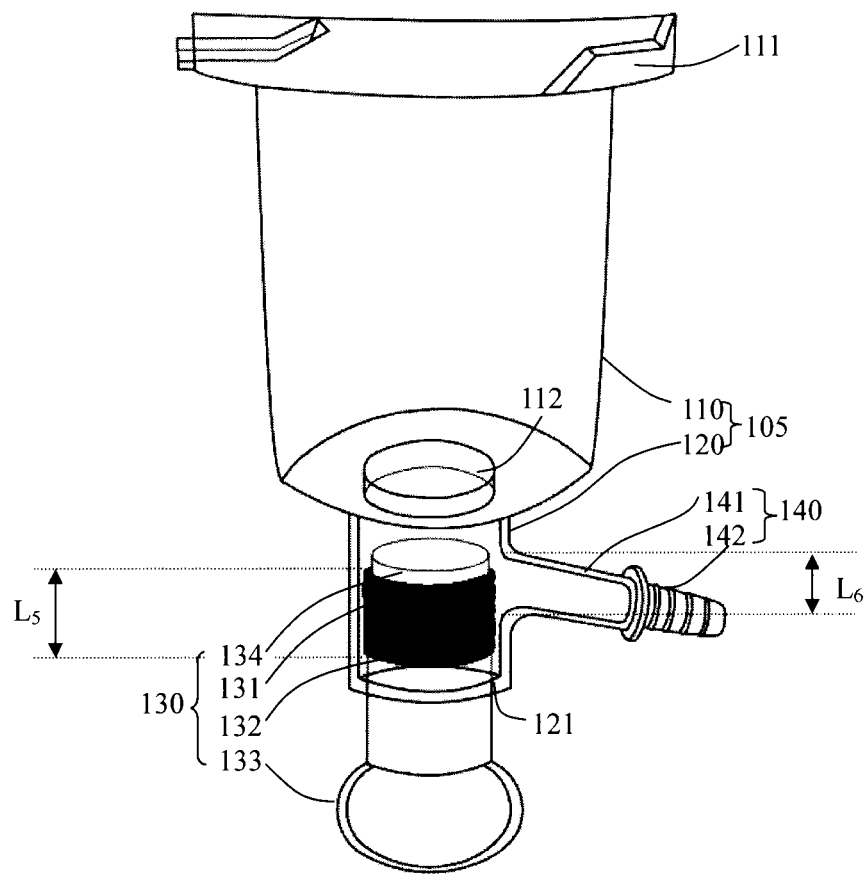

MODIFIED LIQUID TRAP CUP AND A LIQUID TRAP ASSEMBLY

This application claims priority to Taiwan Patent Application No. TW 099214097 filed on Jul. 23, 2010.

CROSS-REFERENCES TO RELATED APPLICATIONS

Not applicable.

BACKGROUND OF THE INVENTION

1. Field of the Invention

The present invention provides a liquid trap cup and a liquid trap assembly using the liquid trap cup, especially a liquid trap cup and a liquid trap assembly using the liquid trap cup employed in the liquid trap device of a medical breathing circuit. In application, the invention can conveniently remove the waste liquid that is collected without disassembling the liquid trap assembly to minimize infections and reduce the burden of the medical staff.

2. Descriptions of the Related Art

Breathing systems are widely used apparatuses in the medical field for facilitating patients' breathing and for providing a clean breathing gas. Thus, besides providing the oxygen needed by the human body, the breathing system is usually used in combination with a humidifier to adjust the humidity of the breathing gas and raise the comfort level during breathing. In addition, the breathing system is capable of dosing respiratory medication to further modify the patient's breathing circulation.

However, in a low temperature environment with cold air, the breathing gas and/or patient's exhaled breath in the breathing circuit will condense in the circuit of the breathing system. Thus, several liquid trap assemblies are normally provided to collect the waste liquid accumulated in the circuit. For example, liquid trap assemblies can be provided at each of the following outlets: the humidifier, the patient's oral/nasal area and the gas cylinder. The waste liquid in the liquid trap assemblies must be cleaned regularly to maintain the function of the breathing system, and prevent bacteria growth and infection.

Currently, many kinds of liquid trap assemblies have been designed. U.S. Pat. No. 4,457,305, for example, disclosed a water trap assembly mainly composed of a lid 510 with an inlet pipe 511 and an outlet pipe 512, a drain member 530 equipped with a value member 531 therein, and a jar 520 with a protruding member 521 therein, as shown in FIG. 1. When the lid 510 is secured on the jar 520, the liquid in the breathing circuit can be collected in the water trap jar 520 through the drain member 530 because the protruding member 521 enables the valve member 531 to open. When the waste liquid in the jar 520 accumulates to a certain level, the jar 520 needs to be disassembled manually to remove the waste liquid. When disassembling the jar 520, part of the inner wall of the water trap assembly is exposed to air, and thus, the germs in the air may attach to the inner wall. After reassembling the jar 520, the germs attached thereon are present in the breathing circuit, thereby increasing the probability of infection. Furthermore, when cleaning the waste liquid, the breathing residue of the patients will come into contact with air and the waste liquid may even spill out, thereby putting the health of family members and medical staff at risk for infection. Presently, in the market, the liquid trap assembly (Model: G-313001) available from VADI Inc. is similar to the above embodiment.

In addition, Taiwan Utility Model Patent No. M376302 disclosed a sealed waste liquid collector for the isolated expiratory system, which forsakes the aforesaid detachable structure and adopts a unitized design as shown in FIG. 2. Briefly, the collector 610 comprises a gas-inlet 611, a gas-outlet 612 and a liquid outlet 620 arranged at the bottom therein. When attempting to discharge the waste liquid in the collector, the cap of the liquid outlet is opened and the liquid outlet is connected with a negative pressure device to drain out the waste liquid. Although such a collector prevents the step of disassembling and emptying, the waste liquid leaks out easily at the moment when the cap is opened and also the liquid outlet is connected with the negative pressure device. However, if the collector is tilted to prevent the leakage of the waste liquid, the waste liquid might flow back and endanger the patients.

In view of the above disadvantages in the prior art, the present invention provides a modified liquid trap cup and liquid trap assembly. While using the liquid trap cup, the waste liquid can be conveniently drained out from its downside without conducting a disassembling and leakage from the system. The liquid trap cup indeed meets the need in the medical industry.

SUMMARY OF THE INVENTION

One objective of the present invention is to provide a liquid trap cup, comprising: a hollow cup tube with an upper portion and a lower portion; a piston element with a top portion and a tail portion, which is arranged airtight in the lower portion and is movable between a start point and an end point of the lower portion; and a liquid discharge structure, which is arranged on a sidewall of the lower portion and between the start point and the end point, and communicates with the lower portion.

Another objective of the present invention is to provide a liquid trap assembly, comprising: a liquid trap cup as mentioned above; and a multi-necked adapter tube with a gas-inlet adapter tube, a gas-outlet adapter tube and a liquid-outlet adapter tube, in which the liquid-outlet adapter tube has an expanded-plate structure that is combined with the liquid trap cup to form a seal structure.

To render the above objectives, technical features and advantages of the present invention more apparent, the present invention will be described in detail with reference to some embodiments hereinafter.

BRIEF DESCRIPTION OF THE DRAWINGS

FIG. 4b and FIG. 4c are cross-sectional views of a liquid trap assembly according to one embodiment of the present invention;

FIG. 6a is a perspective view of a liquid trap assembly according to one embodiment of the present invention;

DESCRIPTION OF THE PREFERRED EMBODIMENT

The following will describe the present invention in detail with reference to the drawings appended. However, the present invention may be embodied in various embodiments and should not be limited to the embodiments described in the specification. In addition, for clarity, the size of each element and each area may be exaggerated in the attached drawings and is not depicted to their actual scale. Furthermore, unless it is additionally explained, the expressions "a," "the," or the like recited in the specification of the present invention (especially in the Claims) should be regarded to comprise the singular and the plural forms.

Figure 1:
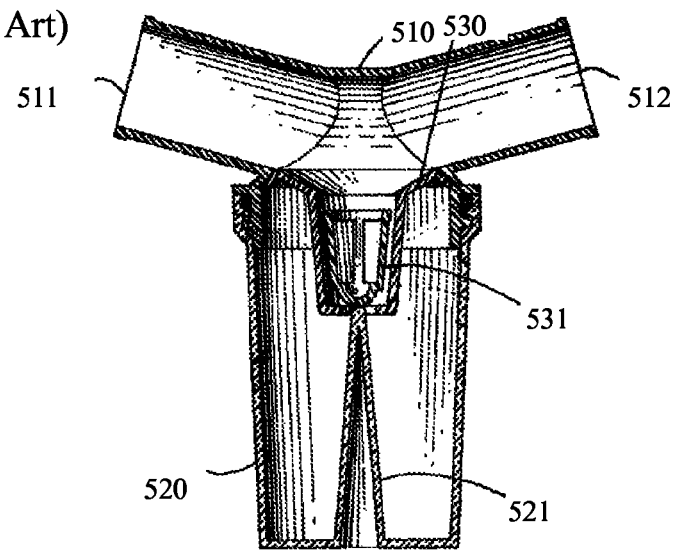
FIG. 1 is a schematic view of a water trap assembly according to the prior art.
Figure 2:
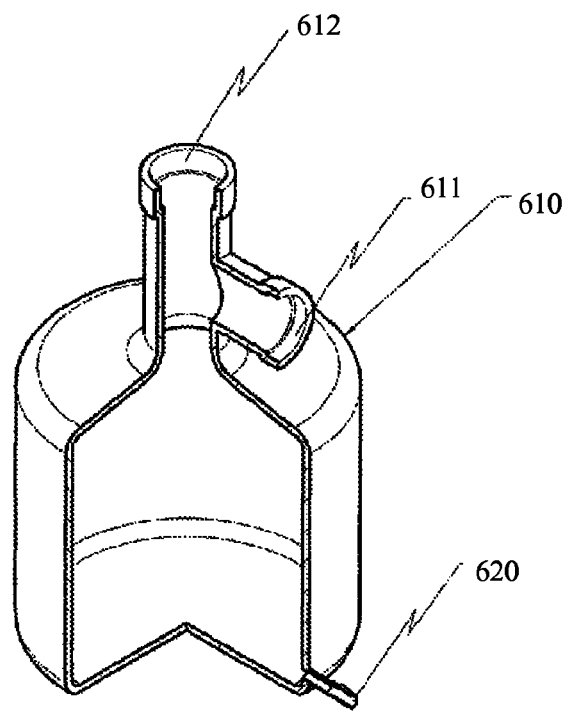
FIG. 2 is a schematic view of a waste liquid collector according to the prior art.
Figure 3A:
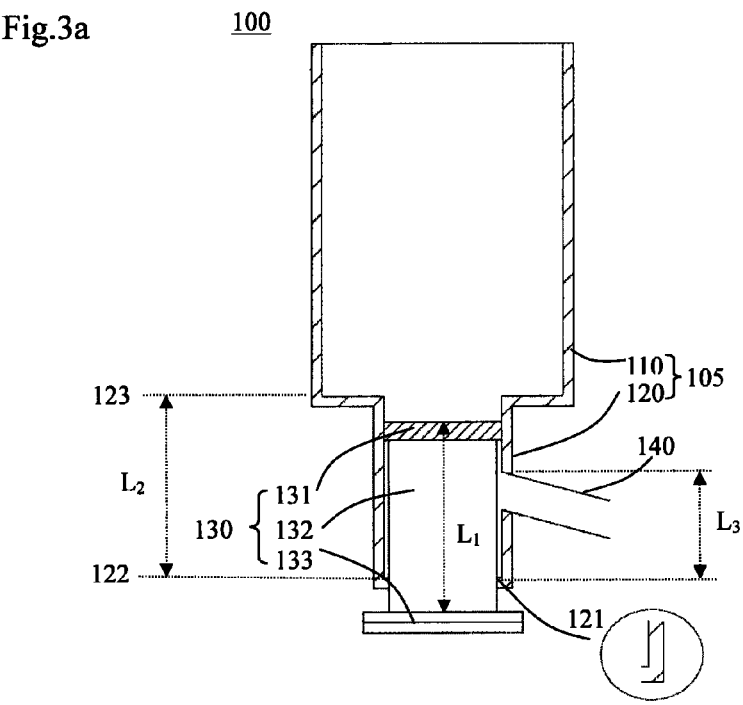
FIG. 3a is a cross-sectional view of a liquid trap cup according to one embodiment of the present invention.

FIG. 3a illustrates a cross-sectional view of a liquid trap 100 according to one embodiment of the present invention. The liquid trap 100 comprises a hollow cup tube 105 (comprising an upper portion 110 and a lower portion 120), a piston element 130 and a liquid discharge structure 140. The piston element 130 has a seal element 131 at its top and a push-pull structure 133 at its bottom, and has a piston rod 133 to connect the seal element 131 and the push-pull structure 133. The diameter of the upper portion 110 may be larger, equal or smaller than that of the lower portion 120, and is preferably larger than the diameter of the lower portion 120 as shown in FIG. 3a. The seal element 131 enables the piston element 130 to be arranged airtight in the lower portion 120. When the piston element 130 moves reciprocally in the lower portion 120 of the hollow cup tube 105, the seal element 131 moves reciprocally between a start point 122 and an end point 123 accordingly.

The material of the seal element 131 is not specially limited except for the impermeability for isolating the liquid. For example, the material of the seal element 131 may be selected from a group consisting of rubber, silica gel, precision ceramics and any known materials used for sealing. In some embodiments of the present invention, the seal element 131 made of rubber is used. Furthermore, the shape of the seal element 131 is also not specially limited. For example, the seal element 131 may be a disc-like covering element, a protruded disc-like covering element, a ring-like covering element, a sleeve-like covering element or the like.

If rubber is used as the seal element 131, a replaceable seal element should be preferably adopted so that the seal element may be optionally replaced to keep the desired airtight effect when the rubber ages and gets damaged after usage for a period of time. That is, the seal element 131 and the piston rod 133 are not unitized. For example, a replaceable, rubber, disc-like covering element 131 may be used to cover the top of the piston rod 132, or use a replaceable, rubber, sleeve-like covering element 131 to cover the whole piston rod 132. When the rubber covering element is aged and damaged, it may be replaced with a new one to provide the desired airtight effect to lengthen the service life of the liquid trap cup 100.

A liquid discharge structure 140 is arranged on the sidewall of the lower portion 120 and between the start point 122 and the end point 123, and communicates with the lower portion 120. When the seal element 131 at the top of the piston element 130 moves to the place between the liquid discharge structure 140 and the end point 123 (including the end point 123), the liquid discharge structure 140 is closed so that the waste liquid in the liquid trap cup 100 cannot pass through the seal element 131 and leak out from the liquid discharge structure 140. When the seal element 131 moves to the place between the liquid discharge structure 140 and the start point 122 (including the start point 122), the liquid discharge structure 140 is opened so that the waste liquid in the liquid trap cup 100 can pass through the liquid discharge structure 140 and be discharged. In this manner, the opening or closing of the liquid discharge structure 140 can be easily controlled by the movement of the piston element 130 to optionally discharge the waste liquid in the liquid trap cup 100 and prevent the undesired leakage of the waste liquid.

Figure 3B:
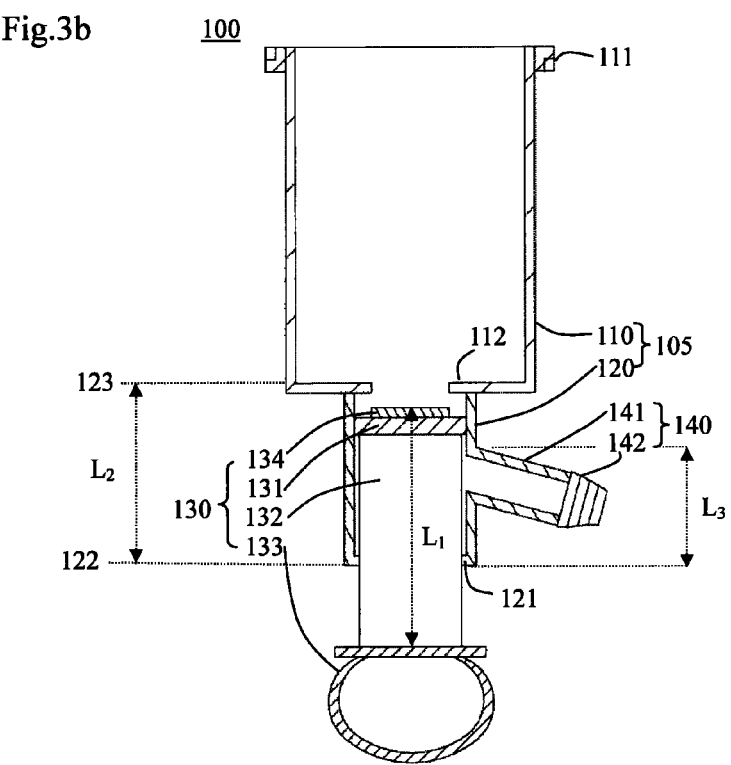
FIG. 3b is a cross-sectional view of a liquid trap cup according to another embodiment of the present invention.

The liquid discharge structure 140 may be in any appropriate form, such as a discharge hole, a discharge valve, a discharge tube or any other structures that can achieve liquid discharge. To facilitate the effect on liquid discharge, the liquid discharge structure 140 may be connected with a negative pressure device while using the liquid trap cup 100. For example, FIG. 3b shows another embodiment according to the present invention, wherein the numerical symbols identical to those shown in FIG. 3a refer to the same elements. In FIG. 3b, the liquid discharge structure 140 of the liquid trap cup 100 comprises a liquid discharge tube 141 and a joint 142. The joint 142 is connected with a negative pressure device to drain the waste liquid conveniently while using the liquid trap cup 100.

According to the present invention, the total length of the piston element 130 is the sum of the "working length $L_1$" and the length of the push-pull structure 133 thereof. The working length $L_1$ should be at least larger than the length $L_3$ (which is the length from the upper end point of the liquid discharge structure 140 at the lower portion 120 to the start point 122) so that the piston element 130 may control the opening or closing of the liquid discharge structure 140 via the seal element 131 as mentioned above. Furthermore, the working length $L_1$ may be equal or larger than the length $L_2$ of the lower portion 120 of the hollow cup tube.

For the liquid trap cup 100 in FIG. 3a, the piston element 130 is well designed so that its working length $L_1$ is equal to the length $L_2$ of the lower portion 120. Thus, it may stop the top of the piston element 130 from exceeding the end point 123 by visual observation to keep the desired airtight effect. Hereinafter, the term "desired airtight effect" means that the waste liquid will not leak out from the liquid discharge structure 140 or the lower portion 120 of the hollow cup tube, and is collected, for example, in the upper portion 110 of the hollow cup tube. In another words, the liquid discharge structure 140 is closed.

In the present invention, the push-pull structure of the liquid trap cup should preferably be a sepal structure or other similar structure. FIG. 3a shows that the liquid trap cup 100 has a sepal push-pull structure 133. Therefore, when pushing the piston element 130 to the end point 123, the piston element 130 can be stopped from moving while the push-pull structure 133 comes into contact with the bottom edge of the lower portion 120. Such a design can prevent the top of the piston element 130 from moving beyond the end point 123 when the piston element 130 is over-pushed, thereby failing to keep the desired airtight effect.

In reference to FIG. 3b, the piston element 130 is well designed so that its working length $L_1$ is slightly larger than the length $L_2$ of the lower portion 120 of the hollow cup tube. There is also a stopping structure 112 set at the bottom of the upper portion 110 of the hollow cup tube (i.e., at the end point 123). Accordingly, the stopping structure 112 does not only control the stop position of the top of the piston element 130 via visual observation, but also controls the piston element 130 to stop at a place without beyond the end point 123 to keep the desired airtight effect conveniently. The position of the stopping structure 112 is not specially limited to that shown in FIG. 3b, and may be also arranged on the sidewall of the lower portion 120 of the hollow cup tube or at any place from the liquid discharge structure 140 to the end point 123.

As mentioned above, the push-pull structure 133 at the tail of the piston element 130 may be optionally designed to enhance the operability of the liquid trap cup of the present invention. The push-pull structure 133, for example, may be sepal-like, rod-like, ball-like, ring-pull or the like. As shown in FIG. 3b, the push-pull structure 133 in the form of ring-pull is used to allow the piston element 130 to move to the start point 122 easily. Also, it is easy to control the desired airtight effect because of the design of the stopping structure 112.

Figure 3C:
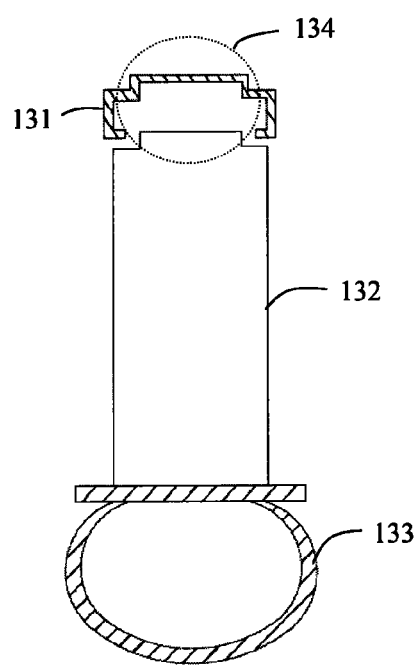
FIG. 3c is a schematic view of a piston element according to one embodiment of the present invention.

The piston element 130 may further comprise a bulge structure 134 as shown in FIG. 3b. Preferably, the bulge structure 134 exactly matches with the stopping structure 112 to further enhance the desired airtight effect when they come into contact with each other. According to the present invention, the bulge structure may be provided via the design of the piston rod and the seal element. In reference to FIG. 3c, the top of the piston rod 133 is designed in a bulge shape and is used together with the seal element 131 correspondingly (preferably made of a flexible material such as rubber) to provide the bulge structure 134.

Furthermore, to prevent the piston element from dismounting from the lower portion of the hollow cup tube while pulling the piston element, a piston-blocking structure can be further arranged to prevent the piston element from moving beyond the start point during use.

For example, as shown in FIG. 3a and FIG. 3b, the lower portion 120 of the hollow cup tube has a piston-blocking structure 121 which is designed as a configuration of an inner-ring corresponding to the structures of the piston rod 133 and the seal element 131 (such as diameter). In combination with the seal element 131 made of a flexible material (such as rubber), the piston rod 133 can pass through smoothly; however, the seal element 131 is fixed by the piston-blocking structure 121. However, when increasing the pull strength, the seal element 131 may be pulled out to replace the seal element 131 optionally.

According to the present invention, the upper portion and the lower portion of the liquid trap cup are connected with each other tightly and may be unitized. The central axis of the upper portion and the central axis of the lower portion may not be collinear, but it is preferable if they are collinear. As shown in FIG. 3a and FIG. 3b, the upper portion 110 and the lower portion 120 of the hollow cup tube 105 are arranged coaxially. The material of the hollow cup tube is not specially limited to a specific material, though is preferred to be selected from a transparent material, such as transparent plastic, for the convenient observation of the change in liquid level.

According to the present invention, as shown in FIG. 3b, the hollow cup tube 105 may further have a latch structure 111 on the outside of the top edge of the upper portion 110 in combination with other components in practical use.

The present invention also provides a liquid trap assembly employing the above liquid trap cup, which can be used in the liquid trap device in the breathing system to patients. The liquid trap assembly comprises a liquid trap cup of the present invention and a multi-necked adapter tube. The multi-necked adapter tube comprises a gas-inlet adapter tube, a gas-outlet adapter tube and a liquid-outlet adapter tube, in which the liquid-outlet adapter tube has an expanded-plate structure to combine with the liquid trap cup to form a seal structure.

Figure 4A:
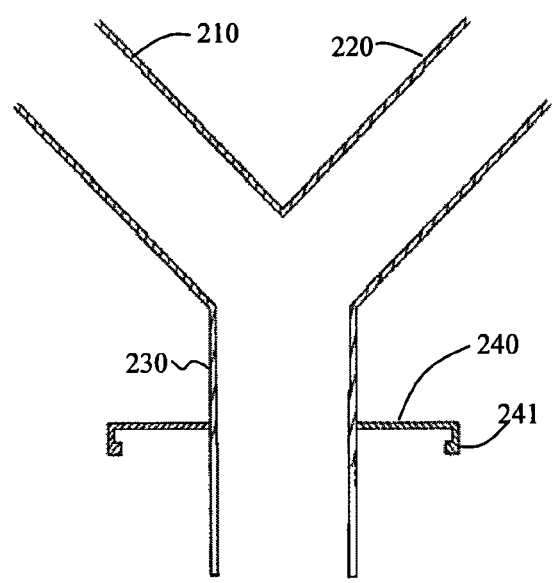
FIG. 4a is a partial enlarged view of a liquid trap assembly according to one embodiment of the present invention.
Figure 4C:
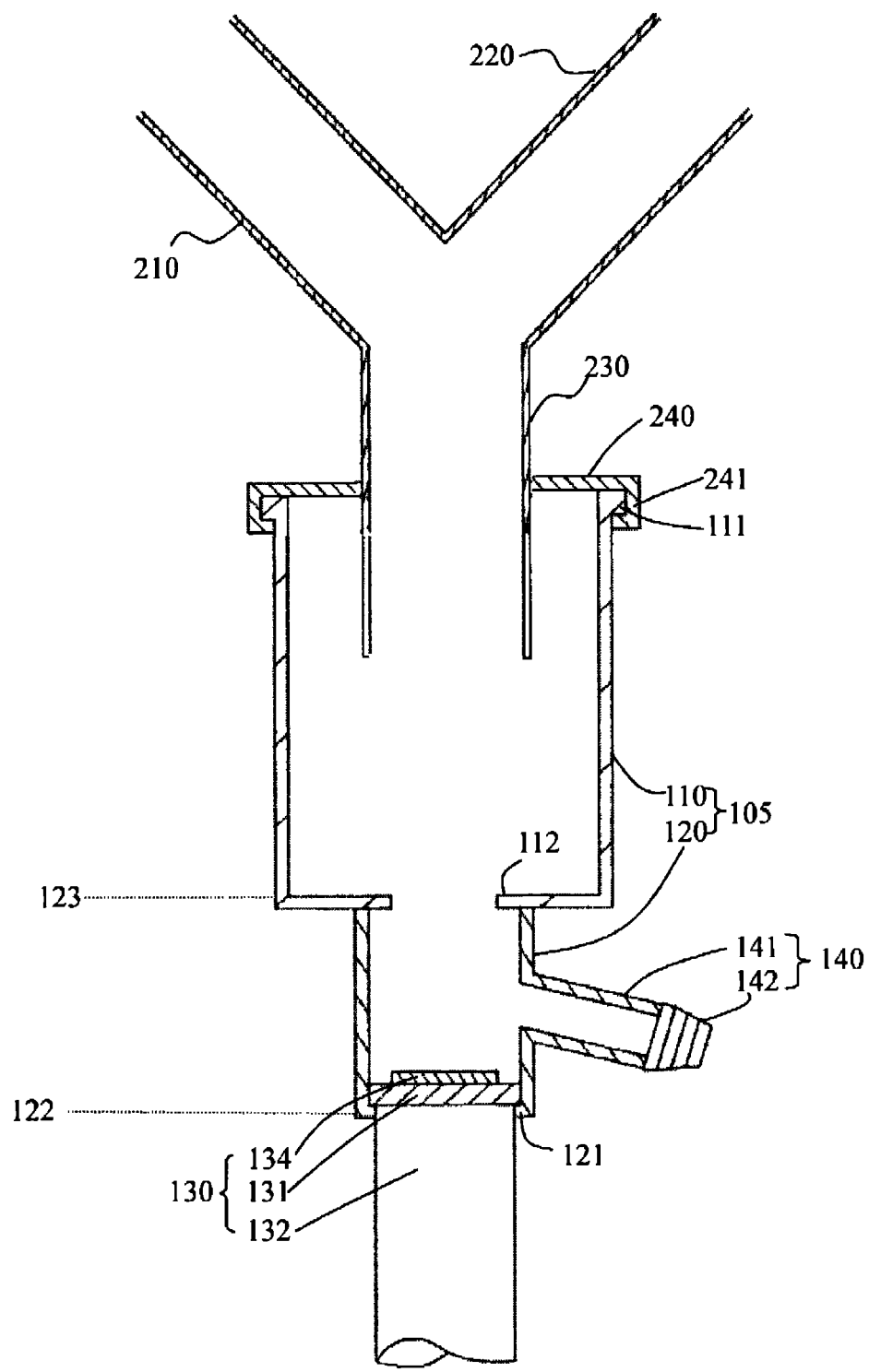

FIGS. 4a to 4c show the cross-sectional views of a liquid trap assembly 200 according to one embodiment of the present invention. FIG. 4a shows a partial enlarged view of the liquid trap assembly 200, FIG. 4b shows the liquid trap assembly 200 used in collecting the liquid and FIG. 4c shows the liquid trap assembly 200 used in discharging the liquid. The numerical symbols identical to those shown in FIG. 3a and FIG. 3b refer to the same elements. As shown in FIG. 4b and FIG. 4c, the liquid trap assembly 200 comprises a liquid trap cup 100 and a multi-necked adapter tube 205 as shown in FIG. 4a. The multi-necked adapter tube 205 comprises a gas-inlet adapter tube 210, a gas-outlet adapter tube 220 and a liquid-outlet adapter tube 230, while the liquid-outlet adapter tube 230 has an expended-plate structure 240. The expended-plate structure 240 has a corresponding latch structure 241 matched with the latch structure 111 on the liquid trap cup 100, so that the multi-necked adapter tube 205 and the liquid trap cup 100 are combined to form a seal structure while using the liquid trap assembly 200.

According to the present invention, a multi-necked adapter tube may be used with different neck numbers depending on the practical requirements and applications, and its shape is not specially limited. In the case of a three-necked adapter tube, it may be a Y-type, T-type or any other appropriate shapes. FIGS. 4a to 4c show a multi-necked adapter tube 205 with three Y-type necks for illustration. Furthermore, according to the present invention, the liquid trap cup and the multi-necked adapter tube may be unitized and thus, do not require a corresponding latch structure and expended-plate structure. However, considering the clean convenience and reusability, the liquid trap cup and the multi-necked adapter tube are preferably separable components. In this case, the liquid trap cup and the expended-plate structure should have correspondingly designed seal structures, such as a pair of latch structures 111, 241 shown in FIGS. 4b and 4c, to prevent the leakage problem of waste liquid caused by, for example, the disassembling of the liquid trap cup. Generally, the seal structure is not specially limited, and may be any appropriate structures known in the art. In addition, the top edge of the upper portion of the hollow cup tube and/or the plate edge of the expended-plate structure of the liquid trap cup may further have a spacer to increase the sealability.

With further reference to FIG. 4b, the gas-inlet adapter tube 210 and the gas-outlet adapter tube 220 are connected with a breathing circuit for passing the breathing gas when using the liquid trap assembly 200. During the trapping of the liquid, the liquid carried in the breathing gas may flow through the liquid-outlet adapter tube 230 by gravity and be collected in the upper portion 110 of the hollow cup tube of the liquid trap cup 100. Meanwhile, the seal element 131 of the piston element 130 may be set at any place from the end point 123 to the liquid discharge structure 140 (including the end point 123); that is, the liquid discharge structure 140 is closed. While attempting to discharge the waste liquid, the piston element 130 is pulled to the start point 122 to open the liquid discharge structure 140 and the waste liquid discharged is gathered for recovery process, as shown in FIG. 4c. After cleaning the waste liquid, the piston element 130 is pushed to the end point 123 to close the liquid discharge structure 140 and return to the state shown in FIG. 4b.

When attempting to remove the waste liquid from the liquid trap cup 100 using the liquid trap assembly 200 as a liquid trap device for the breathing circuit of patients, a negative pressure device can be connected with the joint 142 of the liquid discharge structure 140, and then the piston element 130 is pulled to the start point 122 to open the liquid discharge structure 140. By operating the negative pressure device, the waste liquid is drained quickly, the risk of infection from the waste liquid is minimized, and the burden of the medical staff is significantly reduced. After draining the waste liquid, the piston element 130 is pushed back to the end point 123 to close the liquid discharge structure 140, and finally the negative pressure device is disconnected.

The liquid trap assembly of the present invention may further comprise a valve structure for opening or closing the liquid-outlet adapter tube. Thus, the liquid-outlet adapter tube may be closed during the discharge of the waste liquid to allow the breathing circuit to form a closed system. The useful valve structure may be any appropriate valves, such as a plug valve, a needle valve, a globe valve or the like.

Figure 5A:
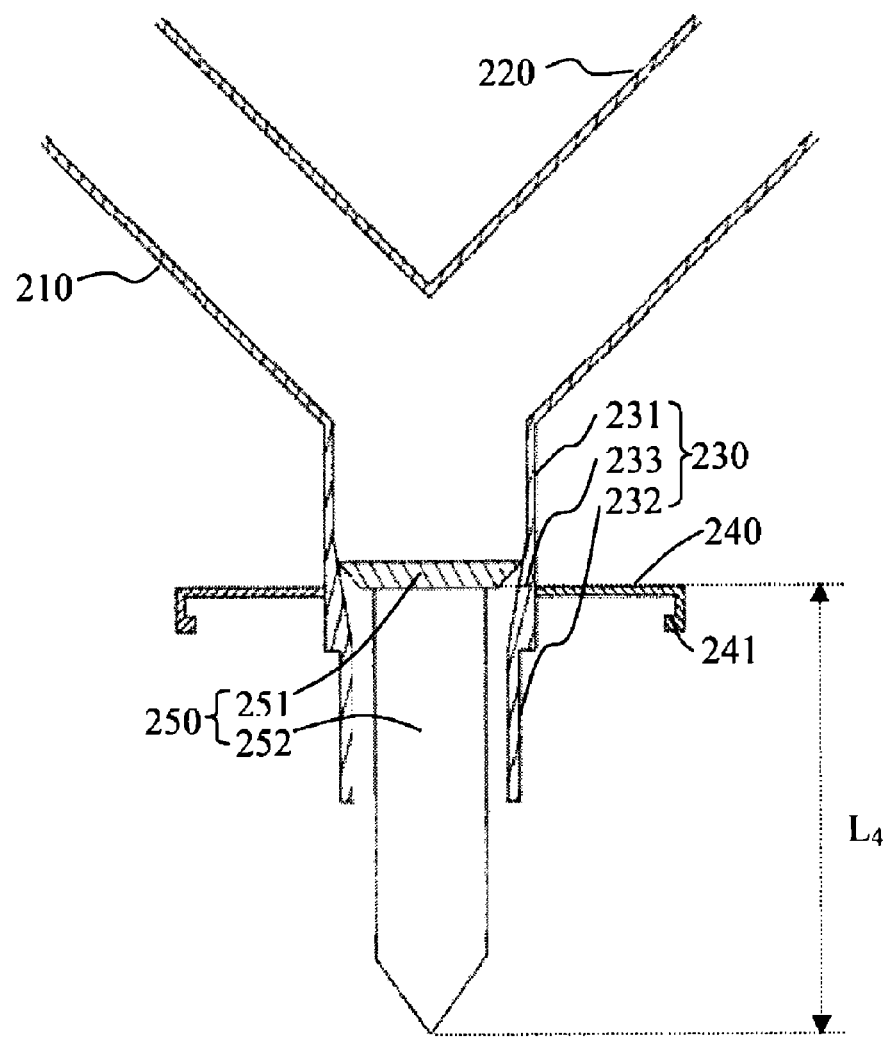
FIG. 5a is a partial enlarged view of a liquid trap assembly with a valve structure according to one embodiment of the present invention.
Figure 5B:
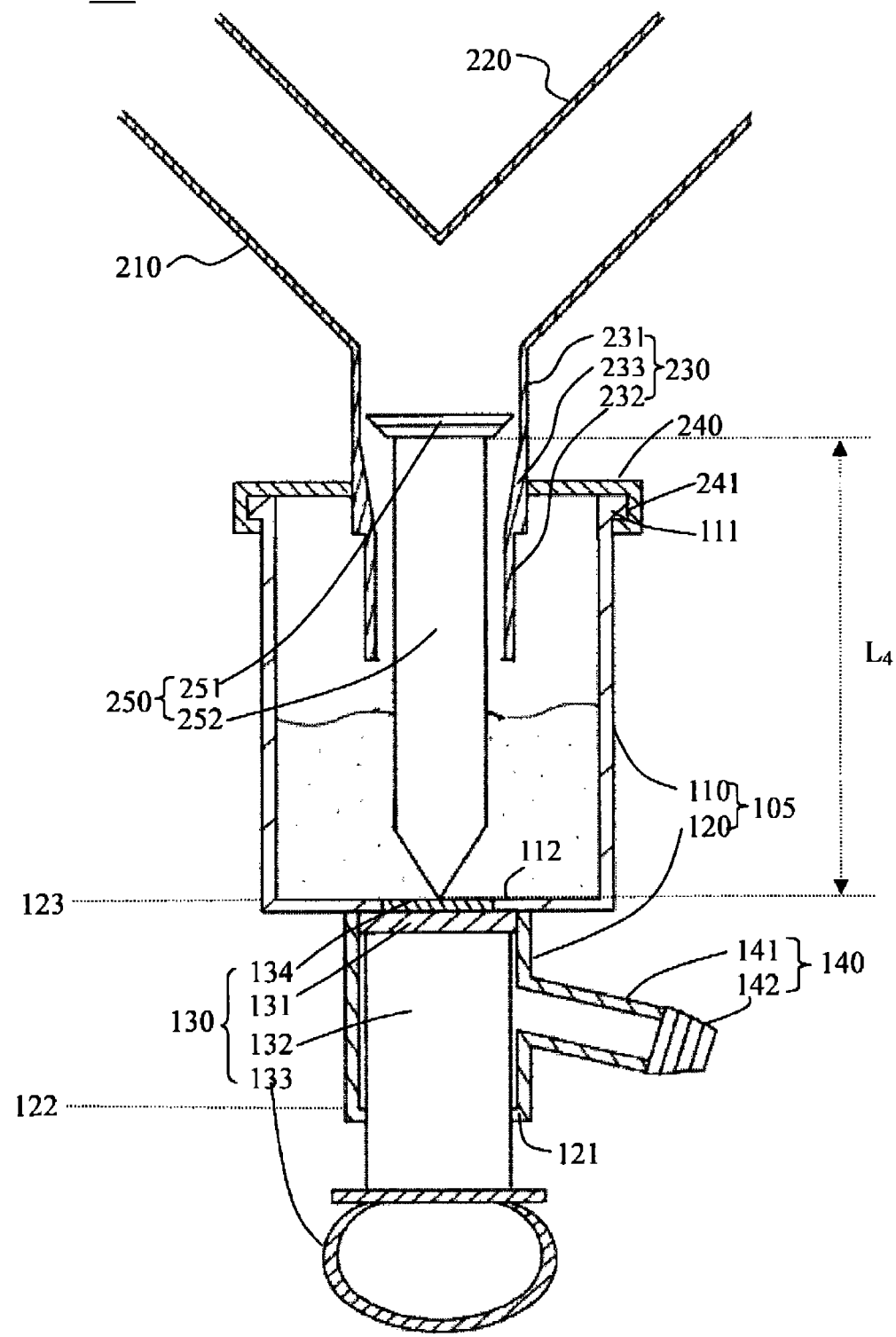
FIG. 5b and FIG. 5c are cross-sectional views of a liquid trap assembly with a valve structure according to one embodiment of the present invention.
Figure 5C:
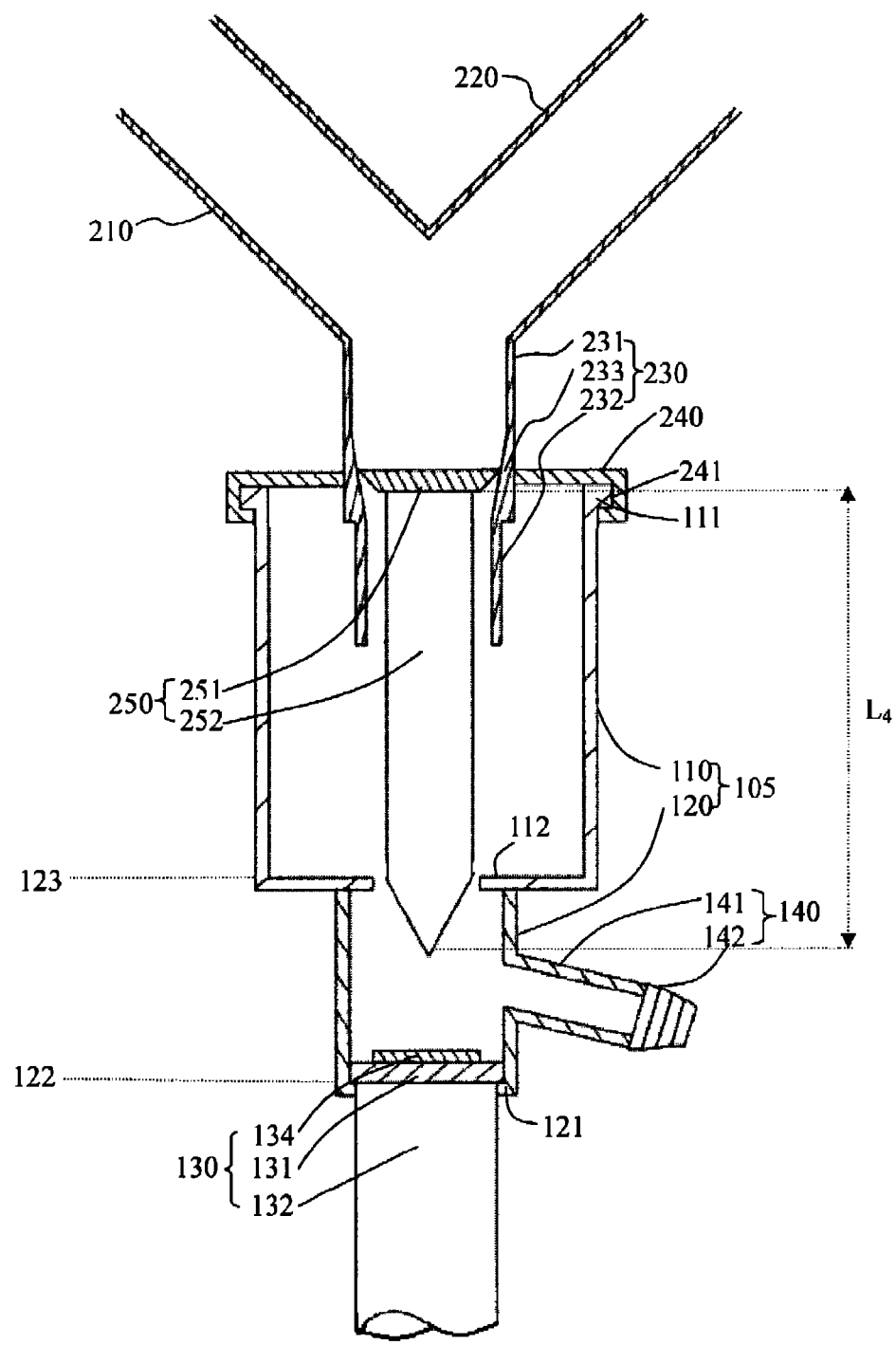

FIGS. 5a to 5c show cross-sectional views of a liquid trap assembly according to another embodiment of the present invention. FIG. 5a shows a partially enlarged view of the liquid trap assembly 200. FIG. 5b shows the liquid trap assembly 200 used in collecting liquid. FIG. 5c shows the liquid trap assembly 200 used in discharging liquid. In these figures, the numerical symbols identical to those shown in FIGS. 4b and 4c refer to the same elements.

The liquid trap assembly 200 comprises a valve structure 250 in the liquid-outlet adapter tube 230 of the multi-necked adapter tube 200 as shown in FIG. 5a. The liquid-outlet adapter tube 230 has an upper adapter tube 231 and a lower adapter tube 232. There is a blocking structure 233 between the upper adapter tube 231 and the lower adapter tube 232. The valve structure 250 comprises a valve end 251 and a tail 252, and is substantially coaxial with the piston element 130. The valve end 251 is embedded in the upper adapter tube 231 by the blocking structure 233 to close the liquid-outlet adapter tube 230 during the discharge of the liquid. The end of the tail 252 can come into contact with the top of the piston element 130 to keep the liquid-outlet adapter tube 230 open during the trapping of the liquid. Therefore, the opening or closing of the liquid-outlet adapter tube 230 is controlled.

When using the liquid trap assembly 200 shown in FIGS. 5b and 5c, the gas-inlet adapter tube 210 and the gas-outlet adapter tube 220 are connected with a breathing circuit for passing the breathing gas. As shown in FIG. 5b, during the trapping of the liquid, the top of the piston element 130 is placed at the end point 123, while the end of the tail 252 (with a designed length L4) comes into contact with the bulge structure 134 of the piston element 130 (in the case without the bulge structure 134, the end of tail 252 directly comes into contact with the seal element 131) to open the liquid-outlet adapter tube 230. Meanwhile, the seal element 131 of the piston element 130 separates the upper portion 110 and the lower portion 120 of the hollow cup tube 105 of the liquid trap cup 100 in airtight. During the discharge of the waste liquid, the piston element 130 is pulled to the start point 122 to open the liquid discharge structure 140 to discharge the waste liquid as shown in FIG. 5c. Meanwhile, the valve structure 250 descends and the tail 252 is separated from the bulge structure 134 of the piston element 130, so that the valve end 251 is blocked by the blocking structure 233 to close the liquid-outlet adapter tube 230. In this manner, the liquid discharge structure 140 is opened and the liquid-outlet adapter tube 230 is closed simultaneously. The liquid discharge structure 140 may also be closed, while the liquid-outlet adapter tube 230 is opened simultaneously through the movement of the piston element 130 and the design of the working length L1 of the piston element 130 and tail rod length L4 of the valve structure 250. Similarly, a negative pressure device may be used in combination to increase the efficiency on discharging the waste liquid, which is described in detail above.

As mentioned above, when opening the liquid discharge structure, the valve structure can descend due to its own weight by gravity. According to the present invention, an elastomer may be further provided in the tail of the valve structure to facilitate the descent of the valve structure with the elastic force and ascertain that the liquid-outlet adapter tube is closed when the liquid discharge structure is opened. Specifically, the aid of the elastomer not only exactly controls the opening and closing of the valve structure, but also prevents incomplete closure caused by the deviation of the valve structure due to shaking or tilting.

According to the present invention, the type of elastomer is not specially limited and may be of any appropriate known materials which are elastic, such as a metal spring, plastic spring, rubber spacer, magnetic set or the like. In some embodiments of the present invention, the metal spring is used.

Figure 6B:
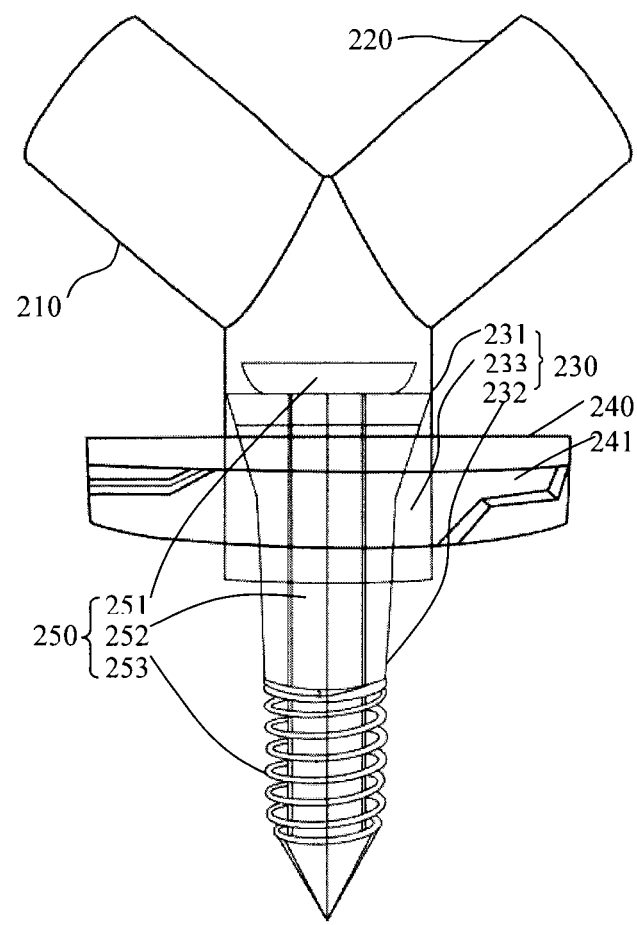
FIG. 6b is a perspective view of a multi-necked adapter tube with a valve structure according to one embodiment of the present invention.
Figure 6C:
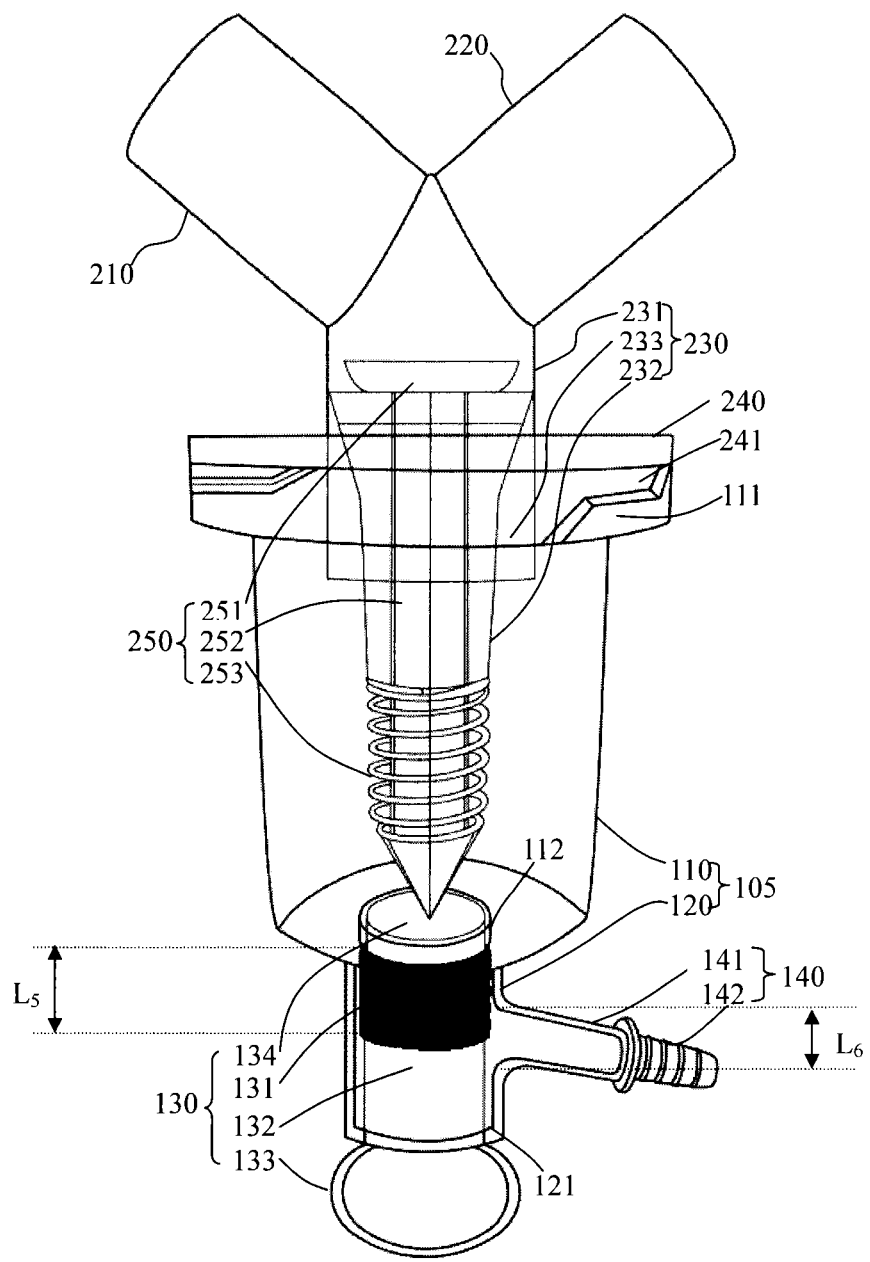
FIG. 6c is a perspective view of a liquid trap assembly with a valve structure according to one embodiment of the present invention.

FIGS. 6a, 6b and 6c are respective perspective views of the liquid trap cup 100, the multi-necked adapter tube 205 having the value structure 250 with an elastomer and the liquid trap assembly 200 according to one embodiment of the present invention. In these figures, the numerical symbols identical to those shown in FIGS. 5a to 5c refer to the same components. The tail 252 is designed as a necking structure and equipped with an elastomer 253 arranged between the end of the tail 252 and the outlet of the liquid-outlet adapter tube 230. Such a configuration may exactly facilitate the opening or closing of the valve structure 250 by the elastic force of the elastomer 253 and improve the function of the valve structure 250.

Furthermore, the liquid trap cup of the present invention can be further designed to prevent the waste liquid collected in the upper portion 110 from leaking out from the opening of the liquid discharge structure 140 and the end of the lower portion 120 (i.e., the position at the piston-blocking structure 121) during the discharge of the waste liquid when the seal element 131 moves to the opening of the liquid discharge structure 140 arranged on the sidewall of the lower portion 120. For example, as shown in FIGS. 6a and 6c, the width $L_5$ of the seal element 131 is designed to be larger than the diameter of the opening $L_6$ of the liquid discharge structure 140, so that the seal element 131 can completely block the opening of the liquid discharge structure 140 when pulling the piston element 130 and prevent waste liquid form leaking out from the end of the lower portion 120. Alternatively, in the case that the width $L_5$ of the seal element 131 is smaller than the diameter of the opening $L_6$ of the liquid discharge structure 140, the piston-blocking structure 121 may be designed as a corresponding seal structure of the seal element 131 and arranged right below the opening of the liquid discharge structure 140 to stop the movement of the piston element 130 while the liquid discharge structure 140 is completely opened. Moreover, the piston rod 133 may be additionally provided with a second seal element (not shown) and the distance between the second seal element and the seal element 131 is at least larger than the diameter of the opening $L_6$ of the liquid discharge structure 140. When pulling the piston element 130 to open the liquid discharge structure 140, the second seal element can seal the waste liquid that flows down from the liquid discharge structure 140 and prevent the waste liquid from leaking out from the end of the lower portion 120.

As described in the above embodiments, the present invention provides a modified liquid trap cup, which may conveniently drain the waste liquid from the downside of the cup and reduce (and may even be free of) the leakage problem of the waste liquid. The present invention also provides a liquid trap assembly using the above liquid trap cup, which can drain the waste liquid without disassembling the assembly and also possess the convenience of being connected with a negative pressure device when discharging the waste liquid.

Although the embodiments practicing the present invention have been described in reference to the drawing appended, the present invention is not limited to those embodiments. Persons skilled in the art can make any amendments or modifications, which should also be encompassed in the scope of the present invention defined in the claims.

What is claimed is:

1. A liquid trap assembly, comprising:
a multi-necked adapter tube with a gas-inlet adapter tube, a gas-outlet adapter tube and a liquid-outlet adapter tube, in which the liquid-outlet adapter tube has an expanded-plate structure that is combined with a liquid trap cup to form a seal structure,
a valve structure to open or close the liquid-outlet adapter tube,
the liquid trap cup, embodied in a liquid trap device of a breathing circuit and comprises:
a hollow cup tube with an upper portion and a lower portion;
a piston element with a top portion and a tail portion, which is arranged airtight in the lower portion and is movable between a start point and an end point of the lower portion; and
a liquid discharge structure, which is arranged on a sidewall of the lower portion and between the start point and the end point, and communicates with the lower portion,
wherein the liquid-outlet adapter tube has an upper adapter tube and a lower adapter tube, and a blocking structure between the upper adapter tube and the lower adapter tube; the valve structure has a valve end and a tail and is substantially coaxial with the piston element, the valve end is embedded in the upper adapter tube by the blocking structure; and during the trapping of liquid, an end of the valve tail comes into contact with the top of the piston element so as to open the liquid-outlet adapter tube and separate the upper portion and the lower portion of the hollow tube of the liquid trap cup.

2. The liquid trap cup of claim 1, wherein the upper portion has a diameter larger than a diameter of the lower portion.

3. The liquid trap cup of claim 1, wherein the piston element has a working length equal or larger than a length of the lower portion.

4. The liquid trap cup of claim 1, wherein the piston element has a seal element at its top.

5. The liquid trap cup of claim 4, wherein the seal element has a width larger than a diameter of an opening of the liquid discharge structure.

6. The liquid trap cup of claim 1, wherein the piston element has a push-pull structure.

7. The liquid trap cup of claim 6, wherein the push-pull structure is a ring-pull.

8. The liquid trap cup of claim 1, wherein the upper portion comprises a stopping structure at its bottom, and when the piston element is moved to the end point, the top of the piston element exactly comes into contact with the stopping structure.

9. The liquid trap cup of claim 8, wherein the piston element further has a bulge structure at its top.

10. The liquid trap cup of claim 1, wherein the liquid discharge structure comprises a liquid discharge tube and a joint, the joint being able to connect with a negative pressure device.

11. The liquid trap assembly of claim 1, wherein the blocking structure is formed by allowing the diameter of the upper adapter tube to be larger than that of the lower adapter tube.

12. The liquid trap assembly of claim 1, wherein the tail of the valve structure is further equipped with an elastomer.

13. The liquid trap assembly of claim 1, further comprising a spacer in a top edge of the liquid trap cup and/or in a plate edge of the expanded-plate structure.

14. The liquid trap assembly of claim 1, wherein the multi-necked adapter tube and the liquid trap cup are unitized.

15. The liquid trap assembly of claim 1, wherein the expanded-plate structure has an inside diameter slightly larger than the outside diameter of a top edge of the liquid trap cup, and corresponding latch structures are arranged in the outside of the top edge of the liquid trap cup and a plate edge of the expanded-plate structure.

* * * * *